(12) United States Patent
Dwork et al.

(10) Patent No.: US 8,876,878 B2
(45) Date of Patent: Nov. 4, 2014

(54) ATTACHMENT MECHANISM FOR STENT RELEASE

(75) Inventors: Joshua Dwork, Santa Rosa, CA (US);
Hubert Yeung, Santa Rosa, CA (US);
Adam Shipley, San Rafael, CA (US)

(73) Assignee: Medtronic, Inc., Minneapolis, MN (US)

( * ) Notice: Subject to any disclaimer, the term of this patent is extended or adjusted under 35 U.S.C. 154(b) by 595 days.

(21) Appl. No.: 12/842,496

(22) Filed: Jul. 23, 2010

(65) Prior Publication Data

US 2012/0022628 A1  Jan. 26, 2012

(51) Int. Cl.
*A61F 2/97* (2013.01)
*A61F 2/95* (2013.01)
*A61F 2/966* (2013.01)

(52) U.S. Cl.
CPC ........... *A61F 2/95* (2013.01); *A61F 2002/9505* (2013.01); *A61F 2/966* (2013.01)
USPC ........................... 623/1.11; 606/108; 623/1.12

(58) Field of Classification Search
CPC .............. A61F 2/95; A61F 2002/9522; A61F 2002/9583; A61F 2002/9586; A61F 2/962; A61F 2/966; A61F 2002/9665
USPC .............. 623/1.11–1.12, 2.11, 2.36; 606/108, 606/191–194, 198
See application file for complete search history.

(56) References Cited

U.S. PATENT DOCUMENTS

| | | | |
|---|---|---|---|
| 5,417,708 A | 5/1995 | Hall et al. | |
| 5,562,698 A | 10/1996 | Parker | |
| 5,601,600 A | 2/1997 | Ton | |
| 5,645,559 A | 7/1997 | Hachtman et al. | |
| 5,733,325 A | 3/1998 | Robinson et al. | |
| 5,817,102 A | 10/1998 | Johnson et al. | |
| 5,876,448 A | 3/1999 | Thompson et al. | |
| 5,891,193 A | 4/1999 | Robinson et al. | |
| 5,935,161 A | 8/1999 | Robinson et al. | |
| 6,077,297 A | 6/2000 | Robinson et al. | |
| 6,136,006 A | 10/2000 | Johnson et al. | |
| 6,168,616 B1 * | 1/2001 | Brown, III | 623/1.11 |
| 6,267,783 B1 | 7/2001 | Letendre et al. | |
| 6,582,451 B1 | 6/2003 | Marucci et al. | |
| 6,673,106 B2 | 1/2004 | Mitelberg et al. | |
| 6,858,034 B1 * | 2/2005 | Hijlkema et al. | 606/108 |
| 7,011,681 B2 * | 3/2006 | Vesely | 623/1.11 |
| 2003/0050694 A1 * | 3/2003 | Yang et al. | 623/2.11 |
| 2004/0143316 A1 * | 7/2004 | Spiridigliozzi et al. | 623/1.13 |
| 2010/0049313 A1 | 2/2010 | Alon et al. | |

FOREIGN PATENT DOCUMENTS

WO   WO 00/71059   11/2000

* cited by examiner

*Primary Examiner* — Christopher D Prone

(57) ABSTRACT

An attachment mechanism for coupling a stent to a delivery system is disclosed. The attachment mechanism is configured to pivot relative to an inner shaft assembly of the delivery system in order to release the stent from the delivery system.

7 Claims, 3 Drawing Sheets

ATTACHMENT MECHANISM FOR STENT RELEASE

BACKGROUND

1. Field of Invention

This disclosure relates generally to medical devices and procedures, and more particularly to a method and system of deploying a stent in a vascular system.

2. Related Art

Prostheses for implantation in blood vessels or other similar organs of the living body are, in general, well known in the medical art. For example, prosthetic vascular grafts formed of biocompatible materials (e.g., Dacron or expanded polytetrafluoroethylene (ePTFE) tubing) have been employed to replace or bypass damaged or occluded natural blood vessels.

A graft tube material supported by a framework is known as a stent-graft or endoluminal graft. In general, the use of stents and stent-grafts for treatment or isolation of vascular aneurysms and vessel walls which have been thinned or thickened by disease (endoluminal repair or exclusion) is well known.

Many stents and stent-grafts are "self-expanding", i.e., inserted into the vascular system in a compressed or contracted state, and permitted to expand upon removal of a restraint. Self-expanding stents and stent-grafts typically employ a wire or tube configured (e.g., bent or cut) to provide an outward radial force and employ a suitable elastic material such as stainless steel or nitinol (nickel-titanium). Nitinol may additionally employ shape memory properties.

The self-expanding stent or self-expanding stent-graft is typically configured in a tubular shape, sized to have a slightly greater diameter than the diameter of the blood vessel in which the stent or stent-graft is intended to be used. In general, rather than inserting it in a traumatic and invasive manner using open surgery, stents and stent-grafts are typically deployed through a less invasive intraluminal delivery, i.e., cutting through the skin to access a lumen or vasculature or percutaneously via successive dilatation, at a convenient (and less traumatic) entry point, and routing the compressed stent or stent-graft in a delivery system through the lumen to the site where the prosthesis is to be deployed.

Intraluminal deployment in one example is effected using a delivery catheter with coaxial inner tube, sometimes called an inner tube (plunger), and an outer tube, sometimes called the sheath, arranged for relative axial movement. The stent or stent-graft is compressed and disposed within the distal end of the sheath in front of the inner tube.

The catheter is then maneuvered, typically routed though a vessel (e.g., lumen), until the end of the catheter containing the stent or stent-graft is positioned in the vicinity of the intended treatment site. The inner tube is then held stationary while the sheath of the delivery catheter is withdrawn. The inner tube prevents the stent-graft from moving back as the sheath is withdrawn.

As the sheath is withdrawn, the stent or stent-graft is gradually exposed from its distal end to its proximal end. The exposed portion of the stent or stent-graft radially expands so that at least a portion of the expanded portion is in substantially conforming surface contact with a portion of the interior of the blood vessel wall.

The distal end of the stent or stent-graft is the end closest to the heart by way of blood flow path whereas the proximal end of the stent or stent-graft is the end furthest away from the heart during deployment. Moreover, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the stent-graft is also the end farthest from the operator (the end farthest from the handle or the handle itself), i.e., the distal end of the catheter and the distal end of the stent-graft are the ends furthest from the handle while the proximal end of the catheter and the proximal end of the stent-graft are the ends nearest the handle. However, those of skill in the art will understand that depending upon the access location, the distal and proximal end descriptors for the stent-graft and delivery system description may be consistent or opposite in actual usage.

Some self-expanding stent and stent-graft deployment systems are configured to have each exposed increment of the stent or stent graft at the distal end of the stent deploy (flare out or mushroom) as the sheath is pulled back. The distal end of the stent-graft is typically designed to expand to fixate and seal the stent to the wall of the vessel during deployment. In some instances, the proximal end of the stent can become stuck on an attachment mechanism coupling the stent to the delivery system. As such, complete release of the stent is prevented.

SUMMARY

Concepts presented herein relate to an attachment mechanism provided within a delivery system for release of a stent from the delivery system. In one aspect, the delivery system is used for percutaneously deploying a stent. The system includes an inner shaft assembly and the attachment mechanism is coupled with the inner shaft assembly and configured to selectively engage the stent. A delivery sheath capsule is slidably disposed over the inner shaft assembly and configured to compressively contain the stent engaged with the attachment mechanism. The attachment mechanism is configured to pivot relative to the inner shaft assembly upon retraction of the delivery sheath capsule to release the stent from the delivery system.

In another aspect, an attachment mechanism for use in a delivery system including an inner shaft assembly and a delivery sheath capsule is disclosed. The attachment member includes a casing coupled to the inner shaft assembly and a lug pivotally coupled to the casing and including fingers for receiving a stent.

In yet another aspect, a method of deploying a stent to an implantation site is provided. The method includes receiving a delivery system loaded with a radially expandable stent, the delivery system including a delivery sheath capsule containing the stent in a compressed arrangement over an inner shaft assembly coupled to the stent through a pivoting attachment mechanism. The stent in the compressed arrangement is delivered through a bodily lumen of the patient and to the implantation site via the delivery system. The method also includes proximally retracting the delivery sheath capsule relative to the stent and pivoting the attachment mechanism to release the stent from the delivery system.

DETAILED DESCRIPTION

The present disclosure generally relates to delivery system for delivering a stent or stent-graft to a deployment site. As used herein, the term "stent" is intended to encompass both stents and stent-grafts. For example, a stent may include a stent frame, a graft tube coupled to a frame, a prosthetic heart valve coupled to a frame, any combinations thereof, etc. The stents or stent grafts comprise frames that have a normal, expanded arrangement and a compressed arrangement for loading within the delivery system. Some embodiments of the frames can be a series of wires or wire segments arranged such that they are capable of self-transitioning from the collapsed arrangement to the normal, radially expanded arrangement. In some constructions, a number of individual wires comprising the frame support structure can be formed of a metal or other material. These wires are arranged in such a way that the frame support structure allows for folding or compressing or crimping to the compressed arrangement in which the internal diameter is smaller than the internal diameter when in the natural, expanded arrangement. In the collapsed arrangement, such a frame support structure can be mounted onto a delivery system. The frame support structures are configured so that they can be changed to their natural, expanded arrangement when desired, such as by the relative movement of one or more sheaths relative to a length of the frame.

The wires of these frame support structures in embodiments of the present disclosure can be formed from a shape memory material such as a nickel titanium alloy (e.g., Nitinol™). With this material, the support structure is self-expandable from the compressed arrangement to the natural, expanded arrangement, such as by the application of heat, energy, and the like, or by the removal of external forces (e.g., compressive forces). This frame support structure can also be compressed and re-expanded multiple times without damaging the structure of the frame. In addition, the frame support structure of such an embodiment may be laser-cut from a single piece of material or may be assembled from a number of different components. For these types of frame structures, one example of a delivery system that can be used includes a catheter with a retractable sheath that covers the frame until it is to be deployed, at which point the sheath can be retracted to allow the frame to self-expand. Further details of such embodiments are discussed below.

Figure 1:
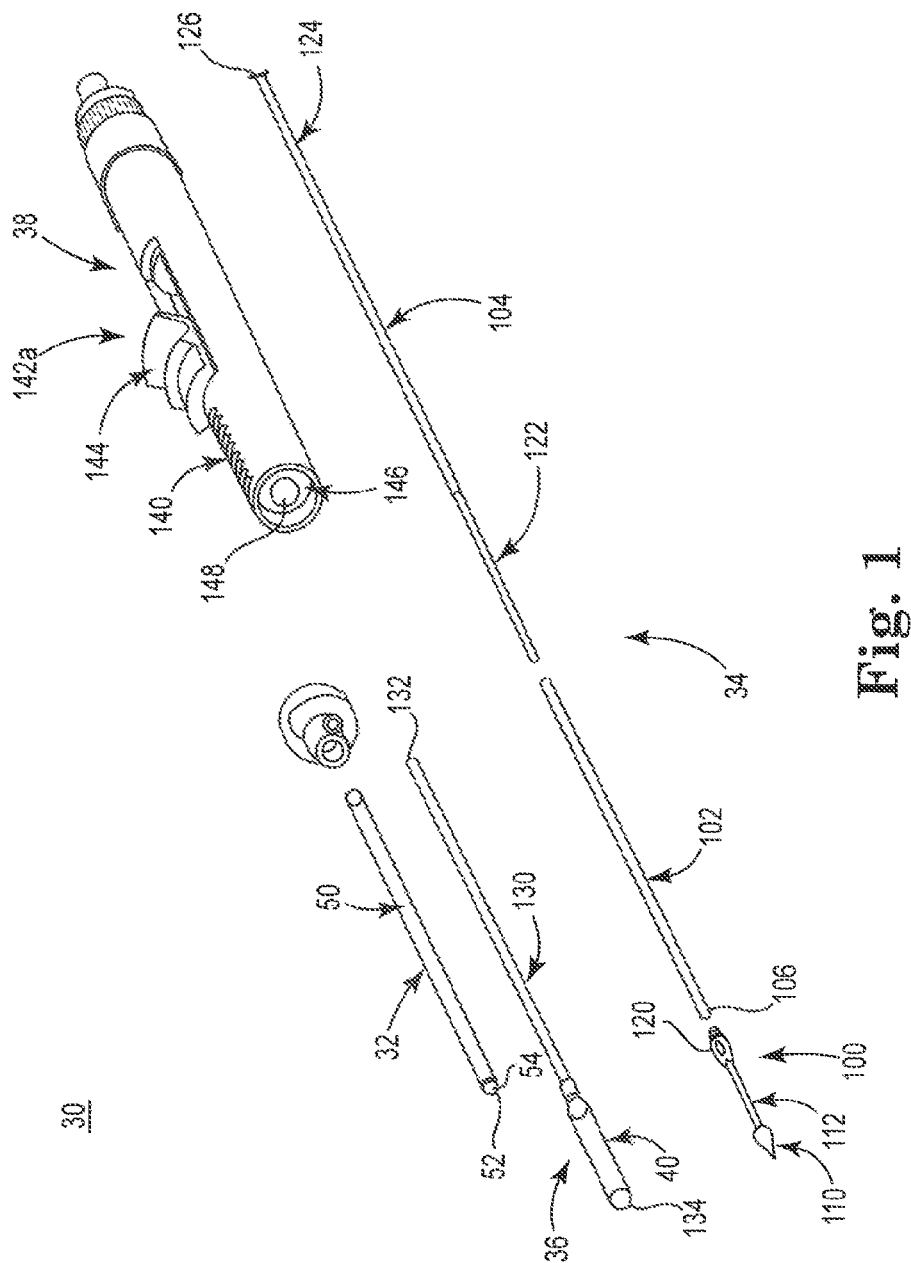
FIG. 1 is an exploded view of an exemplary delivery system.

With the above in mind, one embodiment of a stent delivery system 30 is shown in FIG. 1. The system 30 generally includes a stability layer 32, an inner shaft assembly 34, a delivery sheath assembly 36, and a handle 38. Details on the various components are provided below. In general terms, however, the delivery system 30 provides a loaded state in which a stent (not shown) is coupled to the inner shaft assembly 34 and compressively retained within a capsule 40 of the delivery sheath assembly 36. The delivery sheath assembly 36 can be manipulated to withdraw the capsule 40 proximally from the stent via operation of the handle 38, permitting the stent to self-expand and release from the inner shaft assembly 34. As a point of reference, various features of the components 32-38 reflected in FIG. 1 and described below can be modified or replaced with differing structures and/or mechanisms. Thus, the present disclosure is in no way limited to the stability layer 32, the inner shaft assembly 34, the delivery sheath assembly 36, the handle 38, etc., as shown and described below. More generally, delivery systems in accordance with the present disclosure provide features capable of compressively retaining a self-deploying stent (e.g., the capsule 40) and a mechanism capable of effectuating release or deployment of the stent.

The stability layer 32 illustratively includes a shaft 50, which forms a lumen 52 (referenced generally) sized to be slidably received over the inner shaft assembly 34, terminating at a distal end 54. The shaft 50 can take many forms and in general provides structural integrity to system 30, yet allowing sufficient flexibility to maneuver the capsule 40 to a target site (e.g., the aortic valve). To this end, shaft 50, in one embodiment, is formed of a polymeric material with an associated reinforcement layer. In other embodiments, the stability layer 32 can be eliminated.

The remaining components 34-38 of the delivery system 30 can assume a variety of forms appropriate for percutaneously delivering and deploying a self-expanding stent. For example, the inner shaft assembly 34 can have various constructions appropriate for supporting a stent within the capsule 40. In some embodiments, the inner shaft assembly 34 can include a retention member 100, an intermediate tube 102, and a proximal tube 104. In general terms, the retention member 100 can be akin to a plunger, and incorporates features for retaining the stent within the capsule 40 as described below. The tube 102 connects the retention member 100 to the proximal tube 104, with the proximal tube 104, in turn, coupling the inner shaft assembly 34 with the handle 38. The components 100-104 can combine to define a continuous lumen 106 (referenced generally) sized to slidably receive an auxiliary component such as a guide wire (not shown).

The retention member 100 can include a tip 110, a support tube 112, and an attachment mechanism 120. The tip 110 forms or defines a nose cone having a distally tapering outer surface adapted to promote atraumatic contact with bodily tissue. The tip 110 can be fixed or slidable relative to the support tube 112. The support tube 112 extends proximally from the tip 110 and is configured to internally support a compressed stent generally disposed thereover, and has a length and outer diameter corresponding with dimensional attributes of the selected stent. The attachment mechanism 120 is attached to the support tube 112 opposite the tip 110 (e.g., with an adhesive bond), and is configured to selectively capture a corresponding feature of the stent. The attachment mechanism 120 can assume various forms, and is generally located along an intermediate portion of the inner shaft assembly 34. In some constructions, the attachment mechanism 120 includes one or more fingers sized to be received within corresponding apertures formed by the stent frame (e.g., the stent frame can form wire loops at an end thereof that are received over respective ones of the fingers when compressed within the capsule 40). Moreover, the attachment mechanism 120 includes a pivot mechanism that effectuates release of the stent, as discussed in more detail below.

The intermediate tube 102 is formed of a flexible polymer material (e.g., PEEK), and is sized to be slidably received within the delivery sheath assembly 36. The proximal tube 104 can include, in some embodiments, a leading portion 122 and a trailing portion 124. The leading portion 122 serves as a transition between the intermediate and proximal tubes 102, 104 and thus in some embodiments is a flexible polymer tubing (e.g., PEEK) having a diameter slightly less than that of the intermediate tube 102. The trailing portion 124 has a more rigid construction, configured for robust assembly with the handle 38 such as a metal hypotube, at a proximal end 126. Other constructions are also envisioned. For example, in other embodiments, the intermediate and proximal tubes 102, 104 are integrally formed as a single, homogenous tube or solid shaft.

The delivery sheath assembly 36 includes the capsule 40 and a delivery sheath shaft 130, and defines proximal and distal ends 132, 134. The capsule 40 extends distally from the delivery shaft 130, and in some embodiments has a more stiffened construction (as compared to a stiffness of the delivery shaft 130) that exhibits sufficient radial or circumferential rigidity to overtly resist the expected expansive forces of the stent in the compressed arrangement. For example, the delivery shaft 130 can be a polymer tube embedded with a metal braiding, whereas the capsule 40 is a laser-cut metal tube. Alternatively, the capsule 40 and the delivery shaft 130 can have a more uniform construction (e.g., a continuous polymer tube). Regardless, the capsule 40 is constructed to compressively retain the stent at a predetermined diameter when loaded within the capsule 40, and the delivery shaft 130 serves to connect the capsule 40 with the handle 38. The delivery shaft 130 (as well as the capsule 40) is constructed to be sufficiently flexible for passage through a patient's vasculature, yet exhibit sufficient longitudinal rigidity to effectuate desired axial movement of the capsule 40. In other words, proximal retraction of the delivery shaft 130 is directly transferred to the capsule 40 and causes a corresponding proximal retraction of the capsule 40. In other embodiments, the delivery shaft 130 is further configured to transmit a rotational force or movement onto the capsule 40.

The handle 38 generally includes a housing 140 and one or more actuator mechanisms (i.e., controls) 142 (referenced generally). The housing 140 maintains the actuator mechanism(s) 142, with the handle 38 configured to facilitate sliding movement of the delivery sheath assembly 36 relative to the inner shaft assembly 34. The housing 140 can have any shape or size appropriate for convenient handling by a user. In one simplified construction, a first, deployment actuator mechanism 142a includes a user interface or actuator (e.g., a deployment actuator) 144 slidably retained by the housing 140 and coupled to a delivery sheath connector body 146. The proximal end 132 of the delivery sheath assembly 36 is connected to the delivery sheath connector body 146. The inner shaft assembly 34, and in particular the proximal tube 104, is slidably received within a passage 148 (referenced generally) of the delivery sheath connector body 146, and is rigidly coupled to the housing 140 at proximal end 126.

Figure 2:
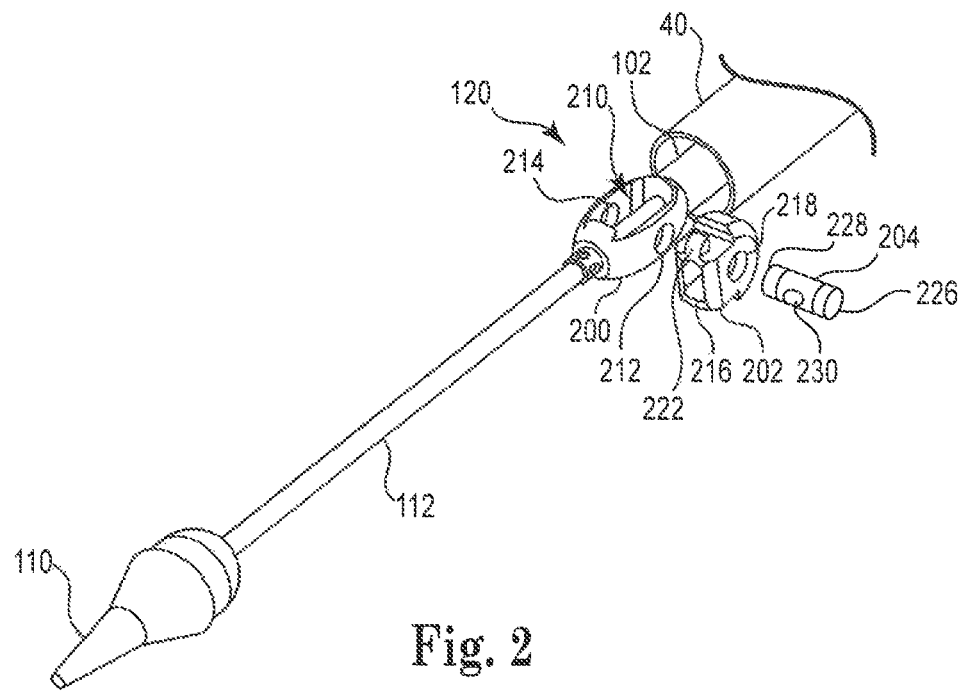
FIG. 2 is a front perspective view of a distal end of the delivery system with an exploded view of an attachment mechanism configured to connect a stent to the delivery system.
Figure 3:
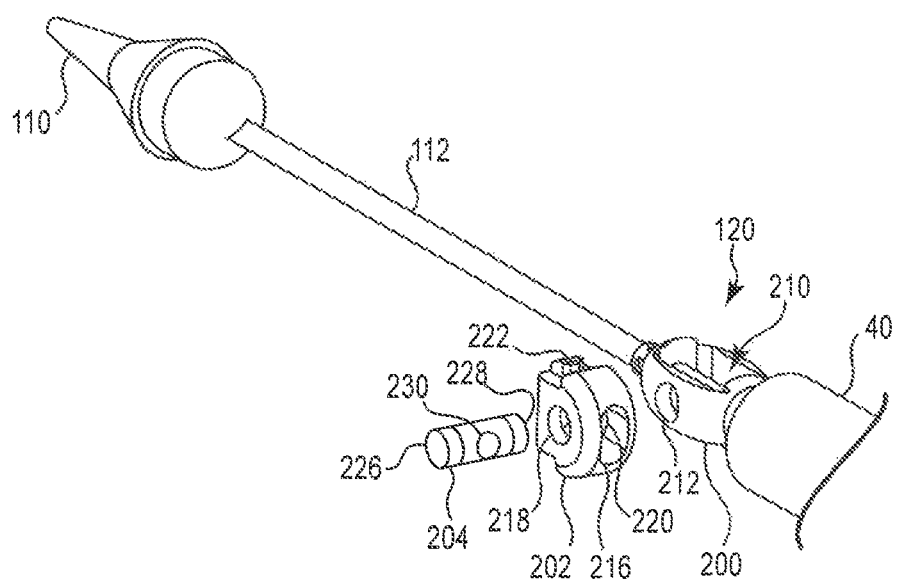
FIG. 3 is a rear perspective view of the distal end of the delivery system with an exploded view of the attachment mechanism configured to connect a stent to the delivery system.
Figure 4:
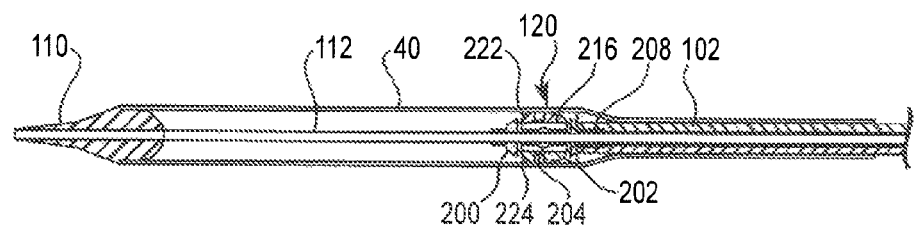
FIG. 4 is a cross-sectional view of the distal end of the delivery system.

As discussed previously, current delivery systems can prevent complete release of stents due to the stent becoming caught on the attachment mechanism 120 as capsule 40 is retracted. In particular, as the stent is delivered, forces (e.g., twisting forces) can cause the frame of the stent to be caught on fingers of the attachment mechanism 120, thus preventing complete release of the stent. With the above in mind, FIGS. 2 and 3 illustrate exploded, isometric views of attachment mechanism 120, which includes a casing 200, pivoting lug 202 and an axle 204 for assisting in release of a stent from the delivery system 30. Additionally, FIG. 4 is a sectional view of the coupling structure assembled within capsule 40. Casing 200 is directly coupled to tube 102 with a suitable fastening element 208 (e.g., exterior threads) positioned within tube 102, which may include internal threads for receiving fastening element 208. Casing 200 further defines a cavity 210 to accommodate pivoting lug 202 and opposed apertures 212 and 214 that receive axle 204.

Lug 202 includes an elliptically shaped slot 216 positioned over support tube 112 and apertures 218 and 220 positioned on either side of slot 216. Furthermore, lug 202 includes fingers 222 and 224, to which a stent can be coupled during delivery. In one embodiment, the stent includes tabs or loops extending from a frame of the stent that are positioned in fingers 222 and 224. In particular, the fingers 222 and 224 are positioned on opposite sides of the lug 202 and define recessed portions to receive loops of the stent frame positioned therein. When compressively contained within capsule 40, the loops of the stent frame are coupled to the fingers 222 and 224. Axle 204 includes opposed ends 226 and 228 configured to form a press or interference fit with apertures 212 and 214 of casing 200, respectively. Additionally, upon assembly, axle 204 passes through apertures 218 and 220 of lug 202. Axle 204 also includes a central aperture 230 for support tube 112 to pass therethrough.

Figure 5:
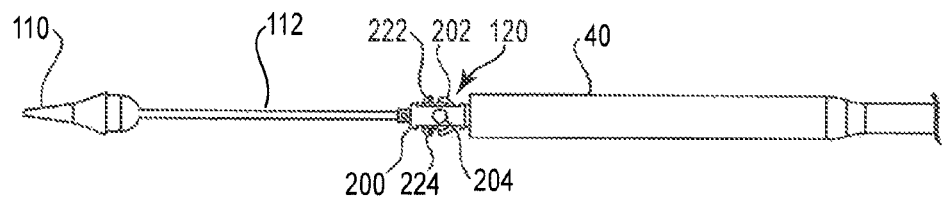
FIG. 5 is a side view of the distal end of the delivery system with an outer sheath retracted.
Figure 6:
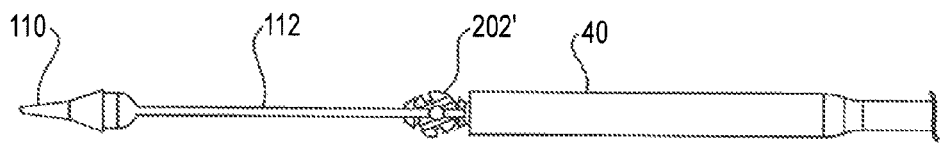
FIG. 6 is a side view of the distal end of the delivery system with a pivoting lug of the attachment mechanism in a first position.
Figure 7:
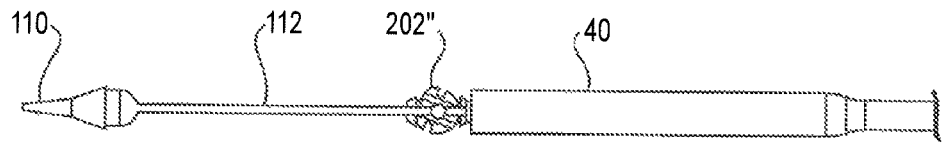
FIG. 7 is a side view of the distal end of the delivery system with the pivoting lug of the attachment mechanism in a second position.

FIGS. 5-7 illustrate the distal end of delivery system 30 with capsule 40 being retracted to expose the attachment mechanism 120. Due to the shape of slot 216 within lug 202, the lug 202 is allowed to pivot relative to the casing 200, for example to a first position 202' (FIG. 6) or a second position 202" (FIG. 7), in which the pivoting lug 202 comes into contact with support tube 112, preventing further rotation of the lug 202 relative to the casing. Forces placed on the lug 202 due to retraction of capsule 40 will cause the lug 202 to pivot about casing 200, effectuating release of a stent coupled thereto. As a result, situations where a stent gets caught on attachment mechanisms 202 can be prevented.

Although the present disclosure has been described with reference to preferred embodiments, workers skilled in the art will recognize that changes can be made in form and detail without departing from the spirit and scope of the present disclosure.

What is claimed is:

1. A delivery system for percutaneously deploying a stent, the system comprising:
an inner shaft assembly including a support tube supporting the stent;
an attachment mechanism coupled to the inner shaft assembly and configured to selectively engage the stent, the attachment mechanism including a casing, a lug positioned within the casing and an axle coupling the casing to the lug, wherein the lug further includes fingers extending therefrom to engage the stent and defines an elongated slot surrounding the support tube to define a range of rotation for the lug about the support tube;
a delivery sheath capsule slidably disposed over the inner shaft assembly and configured to compressively contain the stent engaged with the attachment mechanism;
wherein the lug is adapted to pivot about the axle relative to the inner shaft assembly as the delivery sheath capsule is retracted.

2. The delivery system of claim 1, wherein the lug includes two fingers configured to engage the stent.

3. The delivery system of claim 1, wherein a portion of the stent is positioned between the lug and the delivery sheath capsule.

4. An attachment mechanism for use in a delivery system including an inner shaft assembly and a delivery sheath capsule slidably disposed over the inner shaft assembly, the attachment mechanism comprising:
- a casing positioned around a support tube of the inner shaft assembly;
- an axle coupled to the casing and including an aperture positioned around the support tube; and
- a lug pivotable with respect to the axle and the casing, the lug including fingers defining recessed portions positioned on opposite sides of the lug and adapted to engage a stent.

5. The attachment mechanism of claim 4, wherein the casing includes a fastening element configured to engage the inner shaft assembly.

6. The attachment mechanism of claim 4, wherein the casing includes a cavity and further wherein the lug is positioned within the cavity.

7. The attachment mechanism of claim 4, wherein the lug includes an elliptically shaped slot adapted to accommodate the support tube of the delivery system therein.

* * * * *